(12) United States Patent
Wang et al.

(10) Patent No.: US 12,059,586 B2
(45) Date of Patent: Aug. 13, 2024

(54) WIRELESS RECHARGEABLE AND PORTABLE ANTI-MICROBIAL RESPIRATOR

(71) Applicant: City University of Hong Kong, Hong Kong (HK)

(72) Inventors: Steven Wang, Hong Kong (HK); Ruquan Ye, Hong Kong (HK); Wei Deng, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 552 days.

(21) Appl. No.: 17/458,649

(22) Filed: Aug. 27, 2021

(65) Prior Publication Data
US 2023/0067491 A1  Mar. 2, 2023

(51) Int. Cl.
| | | |
|---|---|---|
| *A62B 7/10* | (2006.01) | |
| *A62B 18/00* | (2006.01) | |
| *A62B 18/02* | (2006.01) | |
| *A62B 18/08* | (2006.01) | |
| *B01D 53/00* | (2006.01) | |

(Continued)

(52) U.S. Cl.
CPC .............. *A62B 7/10* (2013.01); *A62B 18/006* (2013.01); *A62B 18/025* (2013.01); *A62B 18/084* (2013.01); *B01D 53/007* (2013.01); *B01D 53/86* (2013.01); *B03C 3/155* (2013.01); *B03C 3/32* (2013.01); *B03C 3/41* (2013.01); *B03C 3/47* (2013.01); *B03C 3/70* (2013.01); *H02J 50/10* (2016.02); *B01D 2255/104* (2013.01); *B01D 2255/20707* (2013.01); *B01D 2255/20723* (2013.01); *B01D 2255/20761* (2013.01); *B01D 2255/2096* (2013.01);
(Continued)

(58) Field of Classification Search
CPC ........................................................ A62B 7/10
See application file for complete search history.

(56) References Cited

U.S. PATENT DOCUMENTS

| | | | | |
|---|---|---|---|---|
| 2007/0240716 A1* | 10/2007 | Marx | ................... | A62B 18/006 |
| | | | | 128/204.21 |
| 2007/0240719 A1* | 10/2007 | Duarte | ................. | A62B 18/006 |
| | | | | 128/205.27 |

(Continued)

FOREIGN PATENT DOCUMENTS

DE      202020105280 U1 * 11/2020

*Primary Examiner* — Joseph D. Boecker
*Assistant Examiner* — Thomas W Greig
(74) *Attorney, Agent, or Firm* — Idea Intellectual Limited; Margaret A. Burke; Sam T. Yip

(57) ABSTRACT

The present invention provides a wireless rechargeable and portable anti-microbial respirator. The respirator includes a face-piece with an air inlet and an air outlet; a first belt and a second belt, the first belt is connected to ends of the face-piece, and the second belt is configured to wrap around the waist of a user; a flexible outlet tube, where the first end of the flexible outlet tube is connected to the air outlet of the face-piece; a flexible intake tube, where the first end of the flexible intake tube is connected to the air inlet of the face-piece; and a filtration system fixed onto the second belt. The key features of the respirator in the present invention include highly antibacterial and antiviral, long duration, reusable, self-cleaning and self-disinfecting, lightweight and portable, wireless power transfer, and great airflow and comfortable breathing.

19 Claims, 11 Drawing Sheets

(51) Int. Cl.
*B01D 53/86* (2006.01)
*B03C 3/155* (2006.01)
*B03C 3/32* (2006.01)
*B03C 3/41* (2006.01)
*B03C 3/47* (2006.01)
*B03C 3/70* (2006.01)
*H02J 50/10* (2016.01)

(52) U.S. Cl.
CPC .. *B01D 2255/802* (2013.01); *B01D 2259/804* (2013.01); *B03C 2201/26* (2013.01)

(56) References Cited

U.S. PATENT DOCUMENTS

| | | | | |
|---|---|---|---|---|
| 2010/0307332 | A1* | 12/2010 | Yuen | B03C 3/383 |
| | | | | 96/25 |
| 2011/0126828 | A1* | 6/2011 | Wu | B03C 3/155 |
| | | | | 128/205.12 |
| 2020/0346050 | A1* | 11/2020 | Xie | A62B 23/02 |
| 2021/0315297 | A1* | 10/2021 | Brady | A62B 23/02 |
| 2022/0387829 | A1* | 12/2022 | Mattila | A62B 18/006 |
| 2022/0395605 | A1* | 12/2022 | Zhao | A62B 18/025 |

* cited by examiner

US 12,059,586 B2

WIRELESS RECHARGEABLE AND PORTABLE ANTI-MICROBIAL RESPIRATOR

FIELD OF THE INVENTION

The present invention relates to a respirator. In particular, the present invention relates to a wireless rechargeable anti-microbial respirator for healthcare practitioners.

BACKGROUND

In the global COVID-19 pandemic, as of Mar. 31, 2021, in the United States, 455,614 health care workers (HCWs) have been infected with COVID-19, resulting in 1,513 deaths. Some clinical cases have proven that clinicians or nurses who perform intubation are at an extreme risk of exposure to viruses/aerosols because patients may generate a number of small droplets or particles from their respiratory tracks during intubation, and then these droplets or particles spread from the patients' facial region throughout the confines of the operating zone, particularly the particles tend to stick to the lower abdominal region of the health care workers, thus posing the risk of infection. Effective and comfortable masks or respirators are vital, particularly for healthcare workers.

At present, wearing medical masks is an important measure to reduce the risk of cross-infection. However, medical masks still have several limitations, e.g., if masks are disposed of inappropriately, the droplets will remain on the masks, which will increase the risk of secondary transmission; the masks contain plastics, so they are difficult to reuse and recycle, posing an environmental problem; surgical masks are only effective for few hours and may also permit passage of ultrafine viral particles, reducing their efficacy. More importantly, surgical procedures are very delicate, and doctors are required to wear surgical masks to perform operations. However, the structure of the currently-used masks can easily cause the lenses of the glasses worn by the clinicians or nurses to fog due to the heat flow exhaled from the mouth and nose, causing visual disturbances and affecting the operations. Besides, most commercial masks have the problem of being unable to fit tightly to areas on both sides of the nose; even if the mask is designed with a metal clip or other similar elements on the nasal bridge, the effect is still not ideal. Therefore, airborne dust and pathogens have a chance to enter into the masks through the areas on both sides of the nose and then be inhaled by the wearer, thereby causing infection.

Respirators are thus often used to provide better protection for health care workers. Indeed, the US Centers for Disease Control and Prevention (CDC) currently recommends the use of an N95 respirator or other higher level of respirators when performing aerosol generation process (AGP). In Hong Kong, similar advice is given to triage staff with confirmed COVID-19 cases and those involved with AGP.

By using powered air-purifying respirators (PAPRs) with high efficiency particulate air (HEPA) filters, better comfort and a higher level of protection than disposable respirators and N95 respirators can be achieved. PAPRs, however, also have severe limitations. First, while the PAPR is portable, it is bulky and requires the user to wear it as an outer garment. Second, the CDC requires that the PAPRs must be cleaned immediately after each use. Third, most of the HEPA filters are composed of glass or polymer fibers, which only serve to trap droplets. Further, most PAPRs frequently require replacement of their batteries during their lifetime, resulting in environmental problems.

Based on the inadequacies and limitations of medical masks and PAPRs, there is a need to provide an ultra-effective anti-viral or anti-bacterial, long-lasting, reusable, self-cleaning, lightweight and portable respirator as personal protective equipment (PPE) to protect health care workers.

SUMMARY OF THE INVENTION

The main technical problem solved by the present invention is to improve the design of existing respirators. The respirator in the present invention solves the problems of large volume, complicated cleaning process and frequent battery replacement of the traditional respirator.

To solve the technical problems as above-mentioned, the present invention provides a wireless rechargeable and portable anti-microbial respirator. The respirator includes a face-piece with an air inlet and an air outlet; a first belt and a second belt, wherein the first belt is connected to ends of the face-piece, and the second belt is configured to wrap around the waist of a user; a flexible outlet tube, wherein the first end of the flexible outlet tube is connected to the air outlet of the face-piece; a flexible intake tube wherein the first end of the flexible intake tube is connected to the air inlet of the face-piece; and a filtration system fixed onto the second belt. Specifically, the filtration system includes a housing; a first chamber located in the housing, configured to permit exhaled air to flow into the filter system, where the first chamber contains a first channel connected to the second end of the flexible outlet tube, and an upper part of the first chamber is covered by a plate with a plurality of meshes such that only the first channel is exposed, and the meshes are configured to allow fresh airflow to flow into the first chamber; a second chamber located in the housing, configured to permit purified air to flow out of the filter system, where the second chamber contains a second channel connected to the second end of the flexible intake tube, the second chamber further including a light panel and a fan unit; and the first chamber and the second chamber are separated by a filter unit; a third chamber located in the housing, where the third chamber contains a rechargeable battery, an electric motor and a wireless power transfer receiving apparatus. The respirator is configured such that when the exhaled airflow and the fresh airflow flow into the first chamber and are then filtered by the filter unit, the filtered airflow flows into the second chamber and is sterilized by the light panel. The rechargeable battery provides power for the electric motor, and the fan unit is driven by the electric motor for better airflow and for more comfortable breathing.

In accordance with an embodiment, the filter unit is selected from a graphene filter, a bismuth vanadate ($BiVO_4$) filter, or a high efficiency particulate air (HEPA) filter containing at least one ultraviolet-A (UV-A) LEDs and titanium dioxide ($TiO_2$) nanoparticles-coated fiber.

In accordance with an embodiment, the graphene filter further includes two layers of laser induced graphene (LIG) membranes, where a first of the two layers of LIG membranes serves as a positive electrode and a second of the two layers of LIG membranes serves as a negative electrode; and a porous dielectric layer positioned between the two layers of LIG membranes serving as an intermediate layer. The rechargeable battery is connected to the two layers of LIG membranes with one or more wires, and the two layers of LIG membranes with one or more wires. The two layers of LIG membranes and the porous dielectric layer form a parallel plate capacitor, and the rechargeable battery provides the parallel plate capacitor with voltage.

In accordance with an embodiment, the voltage in the parallel plate capacitor is approximately 0.5V to 3V.

In accordance with an embodiment, the $BiVO_4$ filter further includes at least five filtering layers. The at least five filtering layers contain a non-woven layer, an anti-adhesion layer, an activated carbon layer, a molten spray layer and a filter layer. The $BiVO_4$ filter is coupled with a silver (Ag) or copper (Cu) nanoparticle-including layer.

In accordance with an embodiment, the at least one UV-A LEDs has a UV light wavelength in a range of 315 nm to 400 nm.

In accordance with an embodiment, the light panel further includes one or more cluster LEDs and/or one or more wires connected to the rechargeable battery.

In accordance with an embodiment, the shape of the filtration system is a cylinder with a diameter in a range of 50-150 mm and a height in a range of 50-100 mm.

In accordance with an embodiment, the fan unit comprises a fan with a self-adjusting flowrate module.

In accordance with an embodiment, the self-adjusting flowrate module incudes a pressure sensor and a CPU for calculating the required current of the electric motor, and the electric motor and the fan utilize the self-adjusting flowrate module to automatically adjust the rotating speed of the fan based on the pressure within the filtration system.

In accordance with an embodiment, the rechargeable battery provides voltage for two layers of LIG membranes and the at least one UV-A LEDs.

In accordance with an embodiment, the material used for the wireless power transfer receiving apparatus includes one or more copper coils.

In accordance with one embodiment, the face-piece covers mouth and nose of the user.

In accordance with one embodiment, the material used for the face-piece is a silicone material.

In accordance with one embodiment, the wireless rechargeable and portable anti-microbial respirator further including at least one one-way valve positioned at the junction between the face-piece and the first end of the flexible outlet tube and/or the first end of the flexible intake tube to prevent exhaled air with a higher carbon dioxide content from entering the face-piece again, and to prevent exhaled air from flowing directly into the ambient air.

In accordance with one embodiment, the surfaces of both the flexible outlet tube and the flexible intake tube include graphene-based materials, bismuth vanadate ($BiVO_4$) coupled with silver (Ag) or copper (Cu) nanoparticles, or $TiO_2$-based materials.

In accordance with one embodiment, the anti-microbial respirator is an anti-virus respirator or an anti-bacterial respirator.

In accordance with one embodiment, both the flexible outlet tube and the flexible intake tube have an inner diameter of 12 mm and an outer diameter of 15 mm.

In accordance with one embodiment, the flexible outlet tube and the flexible intake tube are further integrated into a sleeve.

The present invention has the following advantages: (1) the improved respirator minimizes the risk of cross-infection, thereby protecting the health care workers; (2) the design and use of highly effective filter units can be used for antibacterial and antiviral applications; (3) the design and production of aerodynamic conditions with positive pressure allow for better airflow and make breathing more comfortable.

Especially, the key features of the respirator in the present invention include highly antibacterial and antiviral, long duration, reusable, self-cleaning and self-disinfecting, light-weight and portable, wireless power transfer, and great airflow and comfortable breathing.

BRIEF DESCRIPTION OF THE DRAWINGS

Embodiments of the invention are described in more details hereinafter with reference to the drawings, in which.

DETAILED DESCRIPTION OF THE INVENTION

In the following description, wireless rechargeable and portable anti-microbial respirators are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

It should be apparent to practitioner skilled in the art that the foregoing examples of the wireless rechargeable and portable anti-microbial respirator are only for the purposes of illustration of working principle of the present invention. It is not intended to be exhaustive or to limit the invention to the precise forms disclosed.

In order to solve the shortcomings of surgical masks or powered air purifying respirators (PAPRs), the present invention provides an ultra-effective anti-microbial respirator, which adopts a novel filtration system to filter the exhaled airflow or external airflow, so as to provide users with fresh and sterile airflow and greatly reduce the risk of infection.

Figure 1:
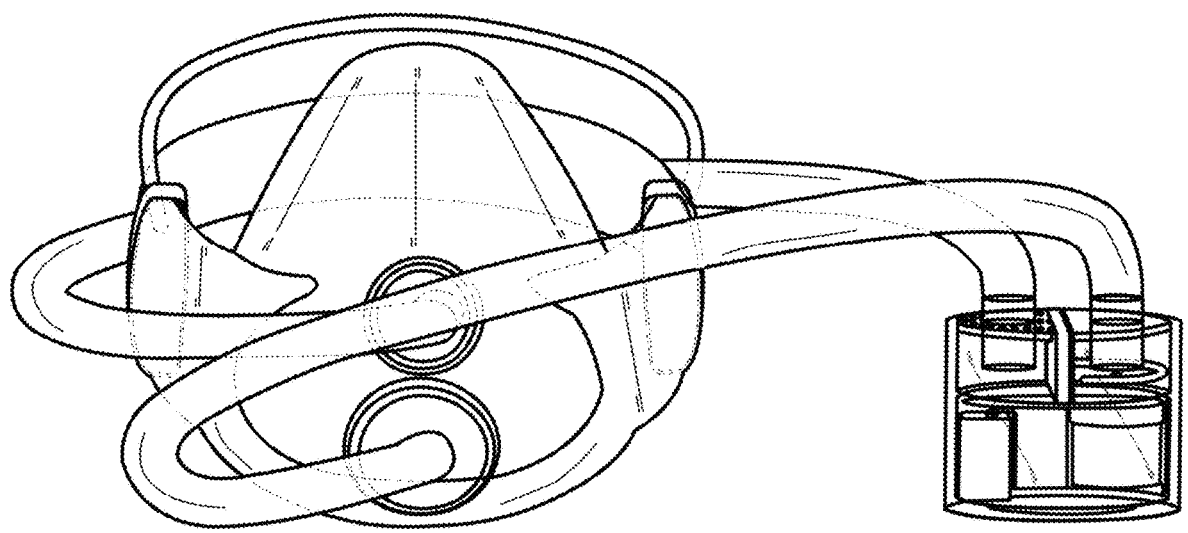
FIG. 1 schematically depicts the structure of the wireless rechargeable and portable anti-microbial respirator according to an embodiment of the present invention.

Turning to FIG. 1, there is provided a wireless rechargeable and portable anti-microbial respirator 100, which includes a face-piece 101 with two openings, one is an air inlet 111 and another one is an air outlet 112; a first belt 102 and a second belt (not shown), in which the first belt 102 is connected to both ends of the face-piece 101, and the second belt is configured to wrap around the waist of a user; a flexible outlet tube 103. The first end of the flexible outlet tube 103 is connected to the air outlet 112 of the face-piece 101. A flexible intake tube 104, has its first end connected to the air inlet 111 of the face-piece 101. A filtration system 105 is fixed onto the second belt. By integrating these components according to the novel design of the invention, the present respirator can be highly anti-microbial, long-lasting, reusable, self-cleaning, lightweight, and portable, which addresses the limitations of current surgical masks, N95 respirators and PAPRs.

In one embodiment, the size of the face-piece is similar to that of N95 respirators (95×145 mm); the face-piece may be made of a flexible polymer such as a silicone-based material that is airtight and flexibly conforms to the face of a user.

In one embodiment, the first and second belts are made of a stretchable material with a width of 1-10 cm and an adjustable length between 55 cm to 120 cm to meet the needs of different users.

In one embodiment, the surfaces of both the flexible outlet tube and flexible intake tube are further coated with photocatalytic materials such as $TiO_2$-based materials and bismuth vanadate ($BiVO_4$) coupled with silver (Ag) or copper (Cu) nanoparticles, or coated with graphene based materials, which can weaken bacteria and viruses on the surface.

In one embodiment, the shape of the filtration system is a cylinder with a diameter in a range of 50-150 mm and a height in a range of 50-100 mm. In addition to the cylinder shape, the filter system can also be set into different three-dimensional shapes, such as cube, tetrahedron, octahedron, cuboid, etc.

In one embodiment, a one-way valve is positioned at the point where the flexible outlet tube and inlet tube respectively enter the face-piece to ensure that the exhaled airflow with higher carbon dioxide content does not enter the face-piece again, preventing the user from rebreathing his/her exhaled air, and ensuring that the user's exhaled airflow does not flow directly into ambient air.

In one embodiment, the wireless rechargeable and portable anti-microbial respirator is an anti-viral respirator. For example, the anti-viral respirator can weaken or kill Coronaviridae, such as Orthocoronavirinae and Letovirinae.

In one embodiment, the wireless rechargeable and portable anti-microbial respirator is an anti-bacterial respirator. For example, the anti-bacterial respirator can weaken or kill gram-positive bacteria and gram-negative bacteria.

Figure 2:
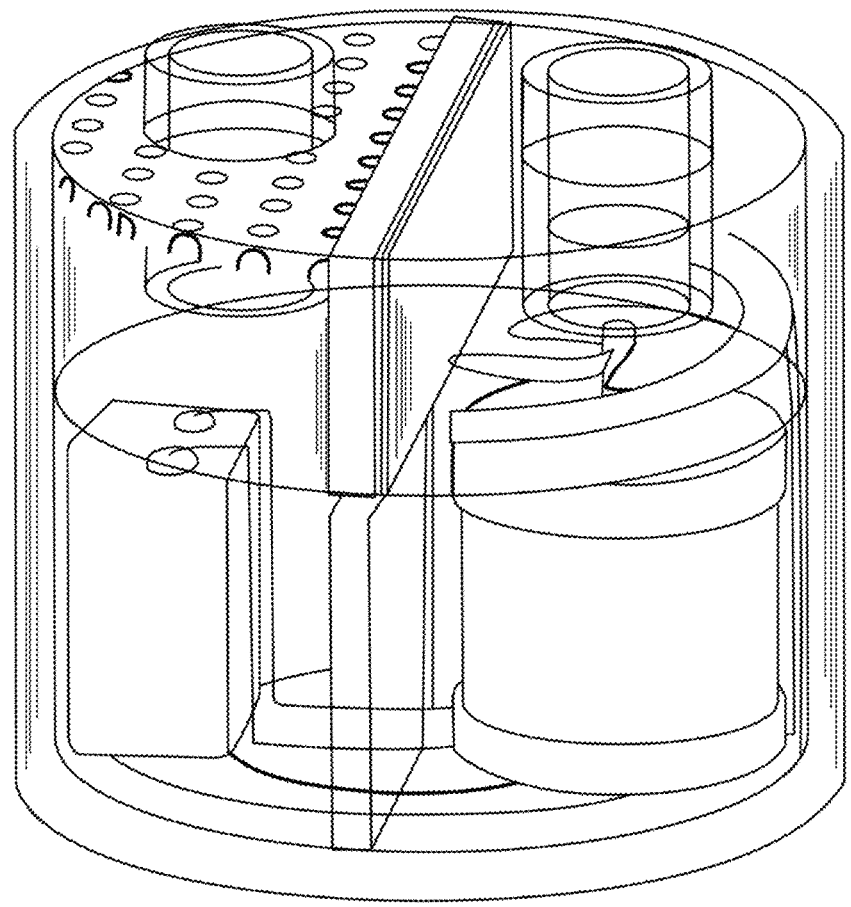
FIG. 2 depicts a perspective enlarged view of the filtration system according to an embodiment of the present invention.

FIG. 2 further shows the internal structure of the filtration system 105. The filtration system 105 includes a housing 201 and three chambers 202, 203 and 204. Specifically, the first chamber 202 is located in the housing 201, allowing exhaled air to flow into the filter system 105. The interior of the first chamber 202 also includes a first channel 211 connected to the second end of the flexible outlet tube 103, and an upper part of the first chamber 202 is covered by a plate 212 with a plurality of meshes 213 and only the first channel 211 is exposed, and the meshes 213 allow fresh airflow to flow into the first chamber 202. The second chamber 203 is located in the housing 201, allowing clean air to flow out of the filter system 105. The inside of the second chamber 203 includes a second channel 221 connected to the second end of the flexible intake tube 104, a light panel 222 and a fan unit 223; the first chamber 202 and the second chamber 203 are separated by a filter unit 205. The third chamber 204 is located in the housing 201. The third chamber 204 includes a rechargeable battery 231, an electric motor 232 and a wireless power transfer receiving apparatus 233. The rechargeable battery 231 provides power for the electric motor 232, and the fan unit 223 is driven by the electric motor 232 for better airflow and for more comfortable breathing. When the exhaled airflow and the fresh airflow flow into the first chamber 202 and are then filtered by the filter unit 205, the filtered airflow flows into the second chamber 203 and is sterilized by the light panel 222.

In one embodiment, the material used for the wireless power transfer receiving apparatus is one or more copper coils. The wireless-charging capability of the present respirator allows quick and convenient charging by simply placing it close to a wireless power transmitter, eliminating the need for constant battery changes. These batteries can, in turn, be charged wirelessly via copper coils housed in the system. In contrast to traditional PAPRs, the respirator of the present invention is less inconvenient for wearing and cleaning, thereby saving time and resources.

The filtration system is the main component of the present respirator. In one embodiment, the filter unit is selected from a graphene filter, a bismuth vanadate ($BiVO_4$) filter, or a high efficiency particulate air (HEPA) filter containing at least one ultraviolet-A (UV-A) LED and titanium dioxide ($TiO_2$) nanoparticles-coated fiber. Graphene based materials and UV-A LEDs combined with $TiO_2$ nanoparticles have each demonstrated usefulness in reducing or eliminating bacteria or viruses. This is because graphene has outstanding super hydrophobicity, self-cleaning, self-reporting, high conductivity and excellent photothermal performances, which can be combined with an electric field to provide more efficient protection. Alternatively, $BiVO_4$ coupled with silver (Ag) or copper (Cu) nanoparticles are known to be responsive to visible light illumination, which has promising antiviral potential. In addition, $TiO_2$ also demonstrates an effective antimicrobial activity when exposed to UV-A light, this is because $TiO_2$ is catalytically active under UV illumination, so that bacteria and viruses are killed or deactivated due to the respective disinfection properties of UVA+ $TiO_2$+ HEPA filter and their mutual reinforcing effect. Accordingly, graphene-based materials and UVA+ $TiO_2$+ HEPA may be integrated to the masks or respirators in producing antibacterial and anti-viral personal protective equipment.

Figure 3A:
FIG. 3A depicts a front view of the simulated user wearing the wireless rechargeable portable antibacterial respirator of the present invention.
Figure 3B:
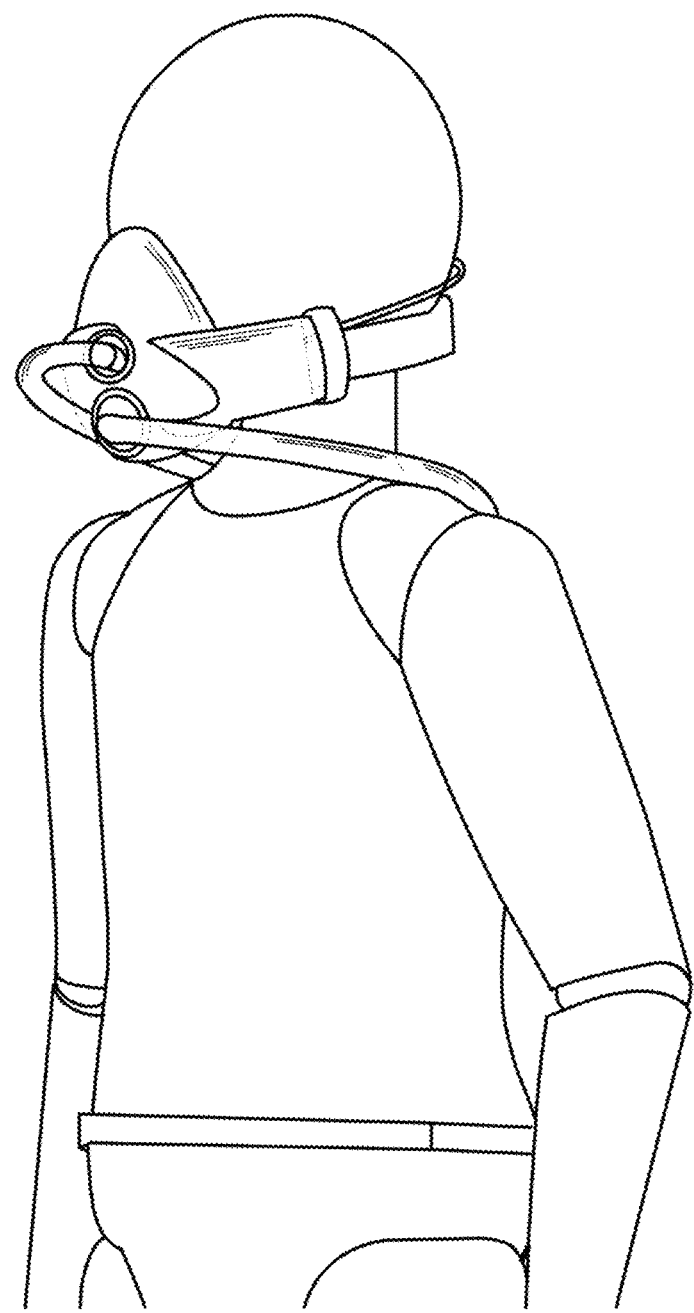
FIG. 3B depicts a side view of the simulated user wearing the wireless rechargeable portable antibacterial respirator of the present invention.
Figure 3C:
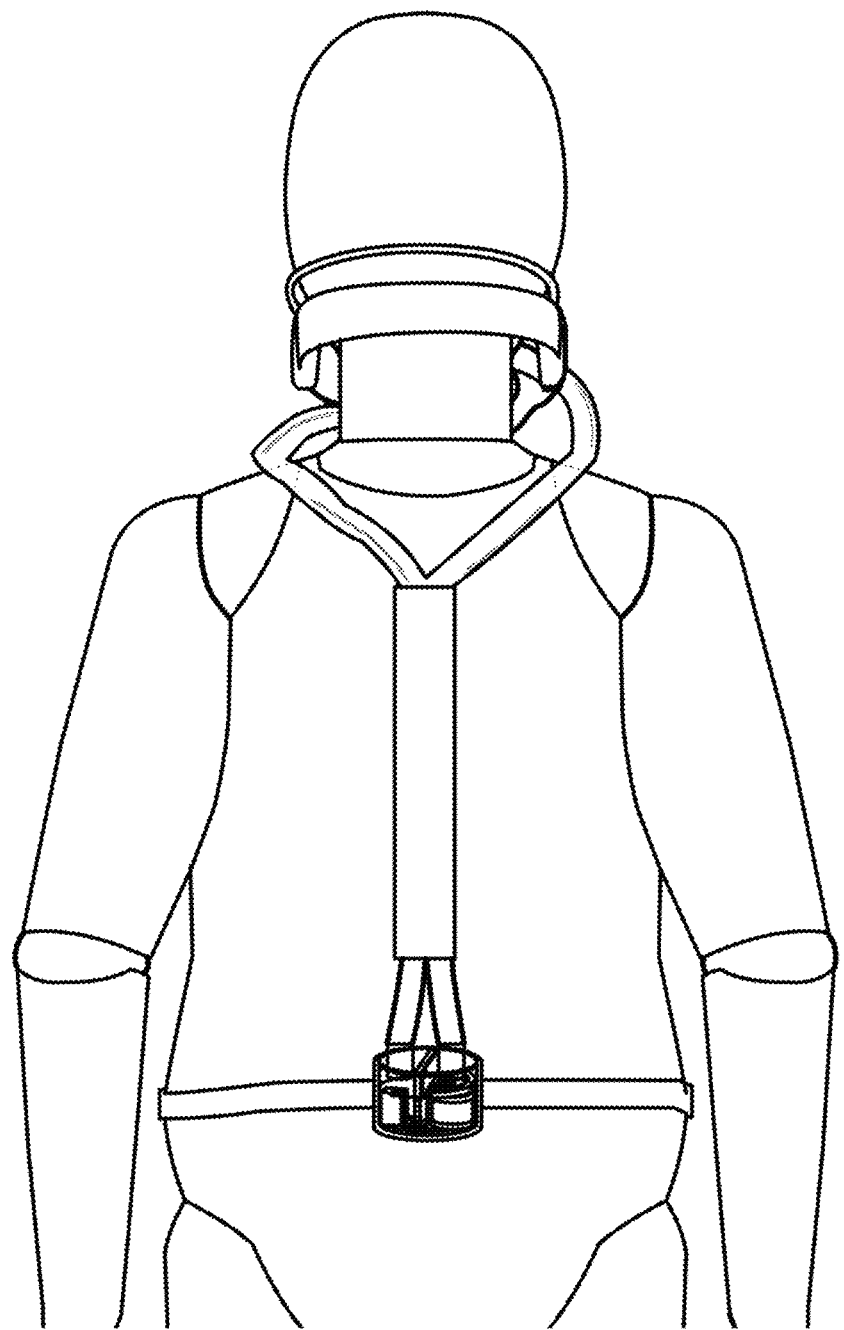
FIG. 3C depicts a rear view of the simulated user wearing the wireless rechargeable portable antibacterial respirator of the present invention.

FIGS. 3A-3C respectively show different views (i.e., front view, side view and rear view) of a simulated user wearing the wireless rechargeable portable antibacterial respirator of the present invention. In addition to being placed on the waist of the user, the second belt fixed with the filtration system can also be placed on other parts of the body, such as arm, chest, or buttock, as long as it does not affect the user's movements.

In another embodiment, both the flexible outlet tube and the flexible intake tube have a length, an inner diameter and an outer diameter tailored to the actual needs of a user. For example, the flexible outlet tube and the flexible intake tube have an inner diameter of 12 mm and an outer diameter of 15 mm. In addition, the flexible outlet tube and the flexible intake tube can be further integrated into a sleeve, as shown in FIG. 3C. Using a sleeve to house the tubes can prevent these long tubes from interfering with the user's movements.

Figure 4:
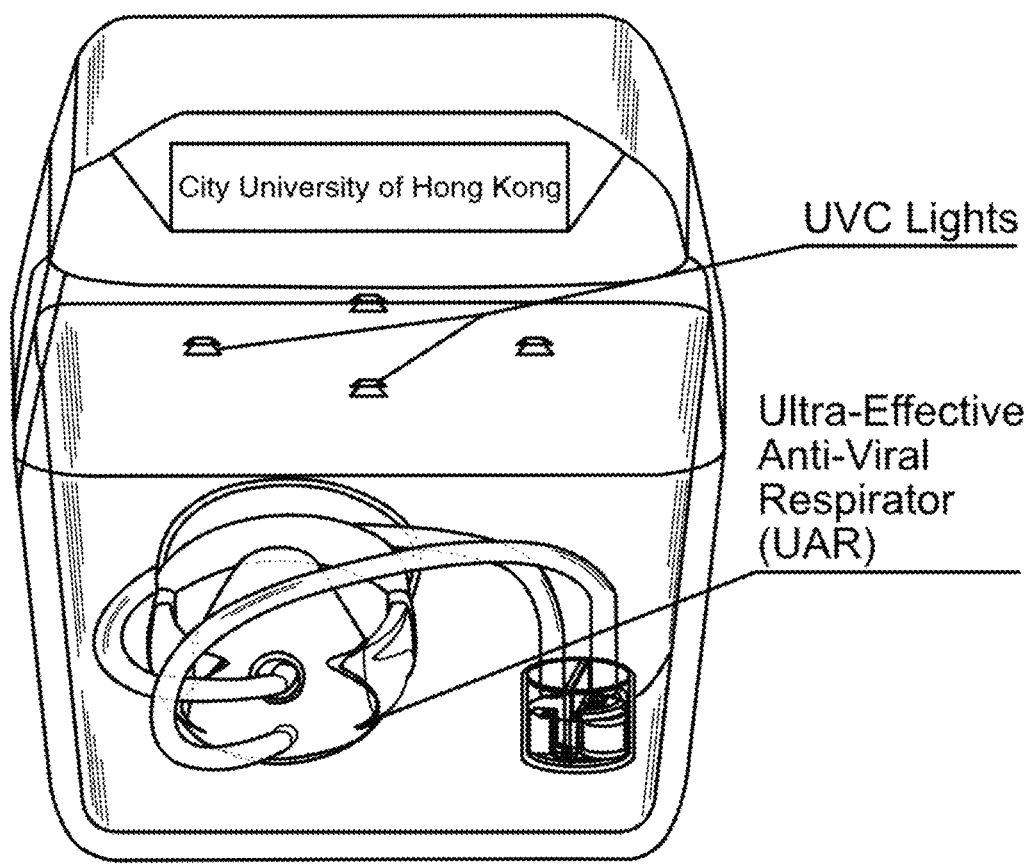
FIG. 4 schematically depicts a wireless rechargeable and portable anti-microbial respirator placed in a sterilizing box for sterilization according to an embodiment of the present invention.

It is known that UV-C is a shortwave ultraviolet light with a wavelength between 100 nm to 280 nm. When various bacteria, viruses, parasites and other pathogens on the surface of the respirator are irradiated with UV-C light, the DNA structures in their cells are destroyed, and the pathogens are thereby killed without using any chemical, thereby achieving the purpose of disinfection and purification. When the respirator of the present invention is not in use, it can be placed in a sterilizing box with one or more UV-C lights for complete sterilization, as shown in FIG. 4. The sterilizing box can safely and quickly sterilize the respirator within 30 seconds, and has an automatic shut-off function.

In one embodiment, the UV-C sterilizing box has a UV light wavelength of 260 nm to 280 nm.

In one embodiment, the UV-C sterilizing box is made by a combination of acrylonitrile Butadiene Styrene (ABS), polycarbonate (PC) and silicone and has a size of 300 mm×300 mm×416 mm.

In one embodiment, the sterilizing box is also wirelessly rechargeable. This eliminates the need for frequent battery replacement.

The following examples illustrate the present invention and are not intended to limit the same.

EXAMPLES

Example 1—Graphene Filter for Filter System 105

The laser-induced graphene (LIG) filter includes primarily two layers of LIG membranes (about 1 mm). These layers act as a positive electrode and negative electrode that respectively stores positive and negative charges from the battery to form a parallel plate capacitor with an electric field, which act as a highly effective air filter to weaken and kill bacteria and viruses. For example, the LIG layers with a weak potential difference form an electric field, which destroys the electrodynamic properties of virus particles and also destroys the infectivity of the coronavirus after contact. Meanwhile, the charge aids in filter design by driving the potentially bacteria and virus-laden droplets and aerosols toward the graphene filter under the imposed electrostatic force. This is due to the fact that droplets and individual microbes in the air usually accumulate significant negative charges due to the high mobility of free electrons in the air, so negatively charged droplets and particles can be carried by the electric field from the fluid to the filter surface.

The present respirator aims to provide better protection by adding LIG's anti-bacterial and anti-viral properties on top of droplet filtration. Furthermore, LIG membranes have a porous structure, resulting in an efficient air filter with minimal pressure drop, providing better comfort. Also, it is more sustainable because battery replacement is minimized due to wireless charging. Further, LIG's self-cleaning mechanisms mean the filter can work for longer and reduce waste. Finally, it is much more portable compared to existing PAPRs.

In one embodiment, the graphene filter includes two layers of laser-induced graphene (LIG) membranes with a thickness of approximately 1 mm, and a porous dielectric layer between the two layers of LIG membranes serving as an intermediate layer. The first of the two layers of LIG membranes serves as a positive electrode and the second of the two layers of LIG membranes serves as a negative electrode (FIG. 2).

In one embodiment, there are insulating dielectric foams between the two LIG membranes to separate the two electrodes and increase the charge density on the surface of the LIG membranes.

In one embodiment, the rechargeable battery provides power to both the motor and the LIG membrane charges. Meanwhile, copper coils are used as wireless power transfer receiving coils to enable charging of the battery.

In one embodiment, the light panel further comprises at least two wires connected to the rechargeable battery. The one or more wires are used to provide voltage from the battery to the two LIG membranes to create an electric field in the parallel plate capacitor. The voltage in the parallel plate capacitor is approximately 0.5V to 3V.

Example 2—$BiVO_4$ Filter for Filter System 105

Bismuth vanadate ($BiVO_4$) coupled with silver (Ag) or copper (Cu) nanoparticles are known to be responsive to visible light illumination. Upon illumination, this photocatalyst undergoes photoexcitation to generate electron and hole pairs. Both of these photogenerated charges are capable of producing reactive oxygen species (ROS) and strongly oxidizing radicals (hydroxyl radicals ·(OH) and superoxide anions ($·O_2^-$) to induce oxidation reaction. With this energetic oxidation potentials, organic substance physically in contact with the particles (e.g., microorganisms) will be oxidized or mineralized. The organic membranes of the microorganism are oxidatively damaged thus providing the antimicrobial properties.

$BiVO_4$ has a narrow optical bandgap, which makes it visible-light activated. Addition of Ag and Cu onto $BiVO_4$ enhances the photoexcited charge transportation and prolongs the charge carrier lifetimes, which typically result in the formation of more ROS for antiviral reaction. In this disclosure, $BiVO_4$—Ag and $BiVO_4$—Cu are selected as active components for their indoor light-induced antiviral properties.

In one embodiment, the design of $BiVO_4$ filter is similar to the graphene filter shown in FIG. 2.

In one embodiment, the light panel further comprises one or more cluster LEDs and one or more wires connected to the rechargeable battery. The cluster LEDs and wires can illuminate the LIG membranes.

In one embodiment, the $BiVO_4$ filter further includes at least five filtering layers, including a non-woven layer, an anti-adhesion layer, an activated carbon layer, a molten spray layer and a filter layer in that order. Further, the $BiVO_4$ filter may be provided with a silver (Ag) or copper (Cu) nanoparticles layer.

Example 3—HEPA Filter Containing at Least One UV-A LEDs and $TiO_2$ Nanoparticles-Coated Fiber for Filter System 105

It is known that UV demonstrates great disinfectant capability against viruses such as COVID-19. UV light destroys the DNA and RNA of germs, thereby eliminating their ability to reproduce and enhancing the killing efficiency and odor elimination. Many hospitals use UV light to sanitize rooms, medical tools, sinks, etc. In addition, as $TiO_2$ has the advantages of high surface activity, strong antibacterial ability, and easy dispersibility, it can be widely applied to textile and pharmaceutical antimicrobial products, especially in masks and air filters in hospitals.

The present HEPA filter with $TiO_2$ nanoparticles-coated fiber layer not only can trap droplets and intercept the tiny dust particles contained in the air passing through the filter screen, but also can inactivate bacteria and viruses by the coated $TiO_2$ nanoparticles. According to the standard established by the United States Department of Energy, the HEPA filter has an efficiency of 99.99% in trapping droplets/particles with a size above 0.3 μm, and the bacteria and viruses attached to the HEPA filter can also be trapped/dehydrated on their surfaces, or inactivated by $TiO_2$ nanoparticles. Moreover, polypropylene fiber is chosen as the material of HEPA filter (the HEPA filter is made of irregular chemical fibers, such as polypropylene fiber, polyester fiber, polyester nonwoven fabric, or glass fiber), with a diameter of about 0.5 to 2.0 microns, so the HEPA filter and $TiO_2$ nanoparticles-coated fibers do not obstruct the airflow. At least one UV-A LED is sealed and enclosed by the HEPA filter and $TiO_2$ nanoparticle fiber and the enclosure; this not only prevents UV-A from irradiating and harming human skin, but also illuminates the internal $TiO_2$ particles, so that these two antibacterial materials (UV-A LEDs and $TiO_2$ nanoparticles-coated fiber) can improve the antibacterial performance of the HEPA filter. This means that in the air filtration system, the two UVA-LEDs located inside are used for disinfection, and under the irradiation of UV light, the $TiO_2$ nanoparticles have a photocatalytic effect to achieve an antimicrobial effect. The HEPA filter containing at least one UV-A LED and $TiO_2$ nanoparticles-coated fiber achieves greater performance and efficiency than the separate utilization of one or two of them, which enables the present respirator to have a higher filtration efficiency of anti-bacteria and anti-viral activity and provide a strong guarantee for the safety of medical staff during the outbreak of epidemic diseases.

In one embodiment, the design of HEPA filter with UV-A LEDs and $TiO_2$ nanoparticles-coated fiber is similar to that of the graphene filter shown in FIG. 2.

In one embodiment, there are 4 wires to providing voltage from the battery to two UV-A LEDs. The rechargeable battery may provide power to both the electric motor in the filter system and the UVA-LEDs.

In one embodiment, the UV-A LEDs have a UV light wavelength in a range of 315 nm to 400 nm.

In one embodiment, copper coils act as a wireless power transfer receiving coil to allow charging of the battery.

For each of the filters described in Examples 1 to 3, in order to get better airflow and more comfortable breathing and forcing the fresh and cleaned air into the flexible intake tube, the fan unit driven by the electric motor provides positive pressure, and the motor is powered by the rechargeable battery.

In one embodiment, the fan unit includes a fan with a self-adjusting flowrate module. The self-adjusting flowrate module further includes a pressure sensor and a CPU for calculating the required current of the electric motor, and the electric motor and the fan utilize the self-adjusting flowrate module to automatically adjust the rotating speed of the fan based on the pressure within the filtration system.

In one embodiment, the interval of the airflow is 2-4 $m^3/h$, which can be adjusted by a control CPU according to user needs and comfort level.

Example 4—Fabrication of Hydrophobic LIG Membrane

A polyimide (PI) film with a thickness of 0.05 mm was provided by Zeman Tape Material Technology, China, and the PI film was irradiated with a 10.6 μm CO2 laser marketing machine in a nitrogen atmosphere. The laser power, speed, and line spacing were set as 1.8 W, 1000 mm/s, and 0.03 mm, respectively.

Figure 5A:
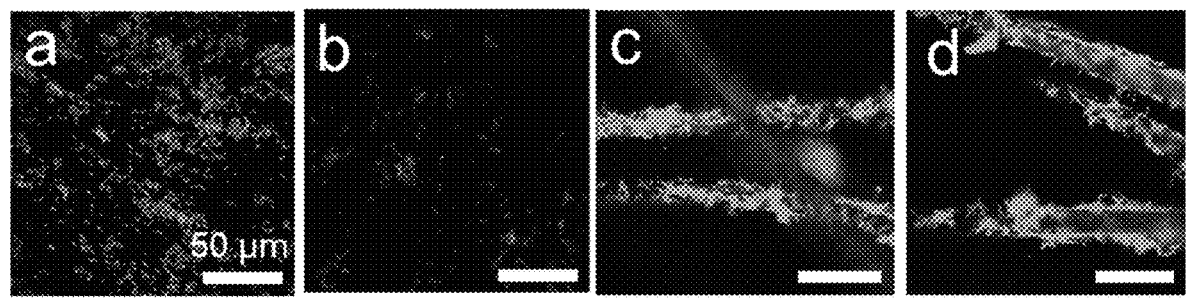
FIG. 5A shows laser scanning confocal microscopy images of graphene (a, b) and control (c, d) stained by bacterial viability kit, where (a, c) were taken after 1 hour incubation, and (b, d) were taken after 8 hours incubation.
Figure 5B:
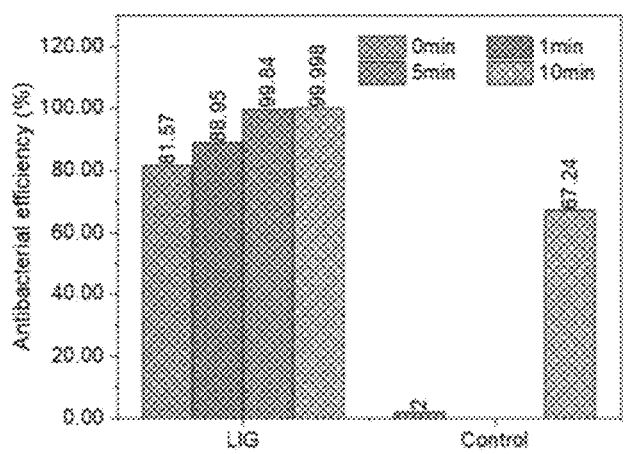
FIG. 5B shows the antibacterial efficiency of LIG membranes after exposure to 0.75 sun irradiation according to an embodiment of the present invention.

The developed LIG membrane is self-sterilizing. The inhibition of infectious species performance can be further enhanced under light. For example, FIG. 5A compares the antibacterial performance of the graphene materials to a polymer surface. It can be seen that most of the bacteria lose their viability after 8 hours in the dark. However, the bacteria on the polymer surface remain alive and little stain was observed (see (b) of FIG. 5A). When quantified by colony forming unit (CFU), the LIG membrane shows an inhibition efficiency of 81.57% in the dark, which increases to 99.998% under 0.75 sun irradiation for 10 minutes. In comparison, the control group has little inhibition capacity (FIG. 5B).

Figure 5C:
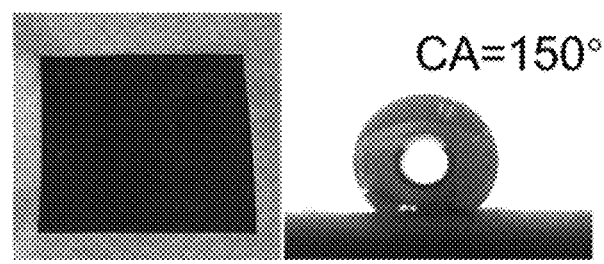
FIG. 5C shows a photo of a graphene sample and its water contact angle according to an embodiment of the present invention.

In one embodiment, the LIG material is scalable, as shown by the 10×10 cm graphene film in FIG. 5C. Moreover, the material is hydrophobic, which can decrease the absorptivity of infectious species (FIG. 5C).

Figure 6A:
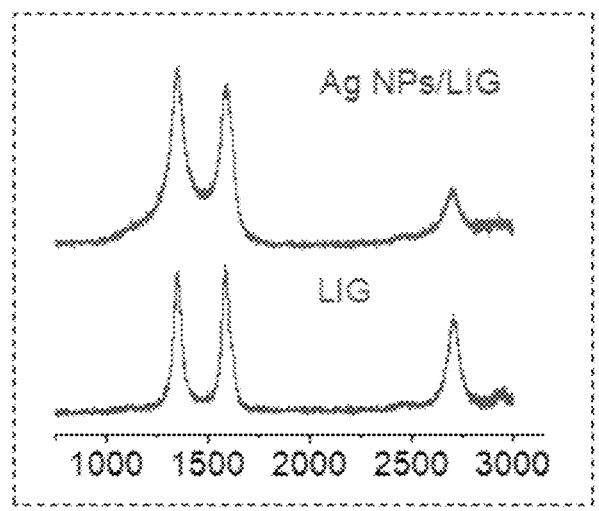
FIG. 6A shows ramen spectrums of laser induced graphene (LIG) membrane and silver (Ag) nanoparticles/LIG membrane.
Figure 6B:
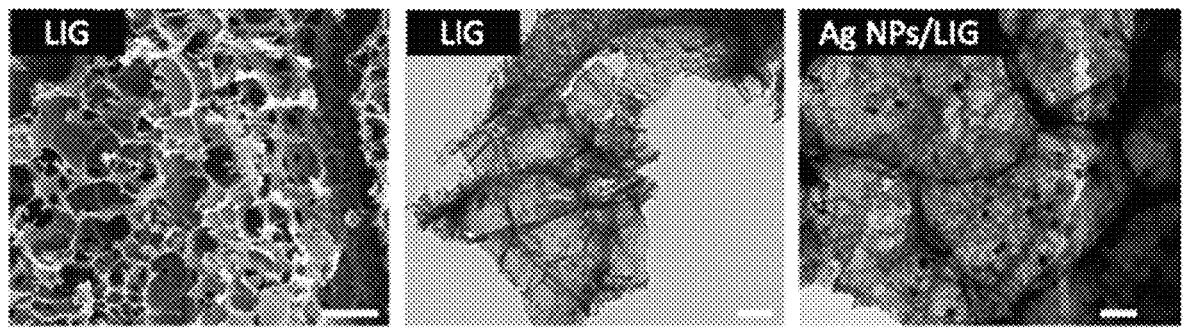
FIG. 6B shows (left) a SEM image of the LIG membrane, (middle) a TEM image of the LIG membrane, and (right) a TEM image of the Ag nanoparticles/LIG membrane.
Figure 6C:
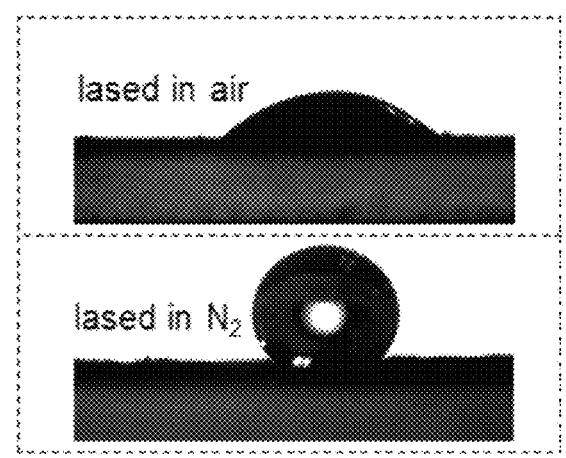
FIG. 6C shows contact angles of LIG membranes prepared in air or in nitrogen atmosphere.
Figure 6D:
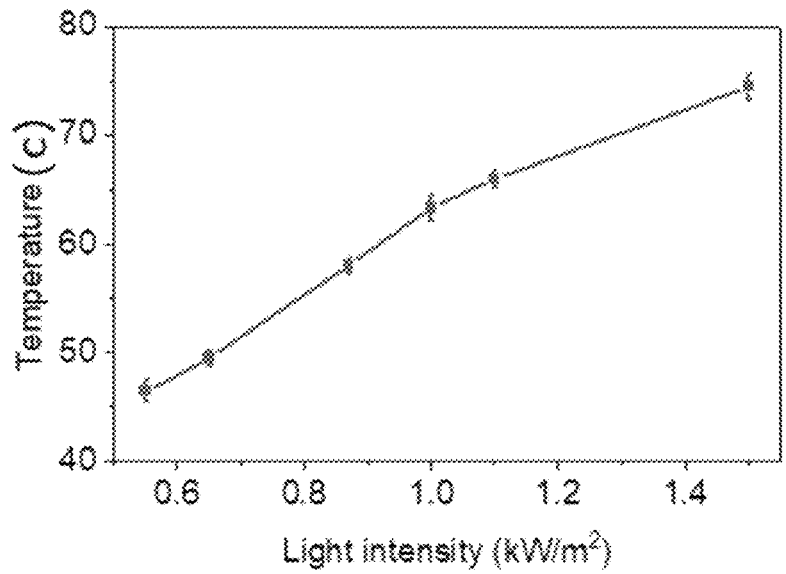
FIG. 6D shows the relationship between temperature and light intensity on a LIG membrane.
Figure 6E:
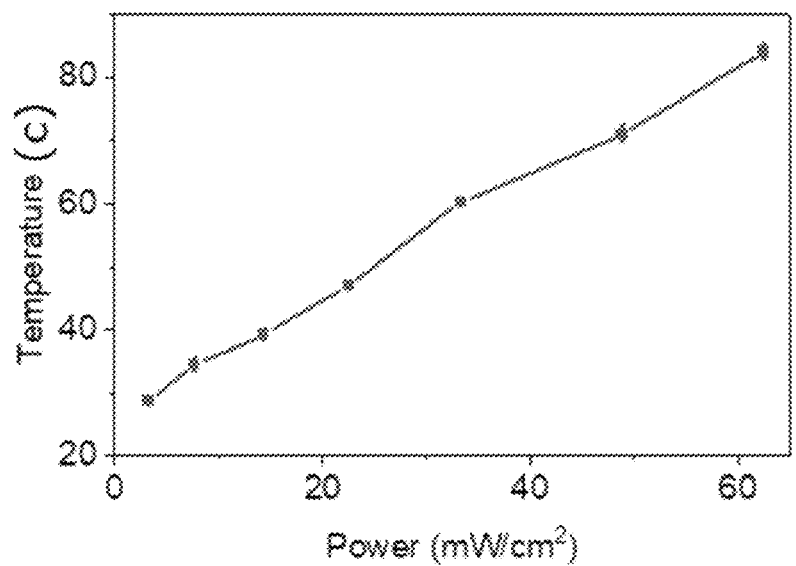
FIG. 6E shows the relationship between temperature and power on a LIG membrane.

Referring to FIGS. 6A-6C, there is provided a LIG membrane with silver. Under normal light, FIG. 6D shows the photothermal effect of the LIG membrane, and FIG. 6E shows the joule effect of the LIG membrane, in which light intensity-dependent or power-dependent change in the temperature can be observed. In addition to the LIG film, the LIG membranes with additional metal demonstrate excellent coronavirus (e.g., HCoV-OC43 and HCoV-229E) resistance. Alternatively, the viricidal efficacy of the hydrophobic LIG (HLIG) against HCoV-OC43 and HCoV-229E can achieve 97.5% and 95%, respectively. Also, the photothermal effect and the hydrophobicity of the HLIG synergistically contribute to the superior inactivation capacity. The stable antiviral performance of HLIG enables its multiple uses, showing advantages in energy saving and environmental protection. A temperature of 46° C., which is sufficient for the virus inactivation, may be achieved by applying direct current power ($\approx$20 mW $cm^{-2}$). This temperature can be easily attained by using 2 or 3 AA batteries.

Figure 7A:
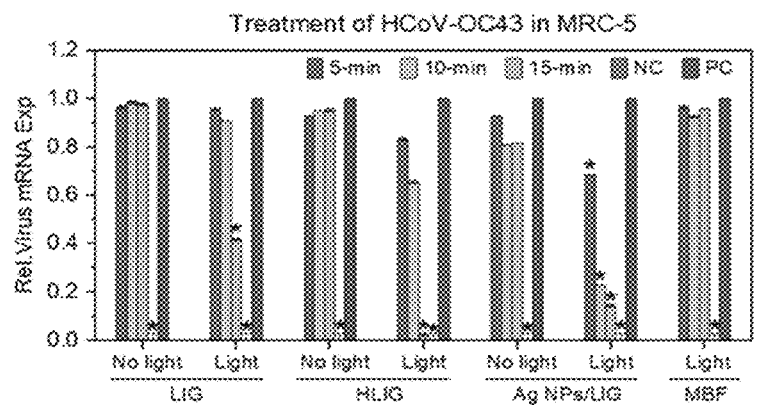
FIG. 7A shows anti-viral effect of different LIG membranes on MRC-5 cells infected with HCoV-OC43.
Figure 7B:
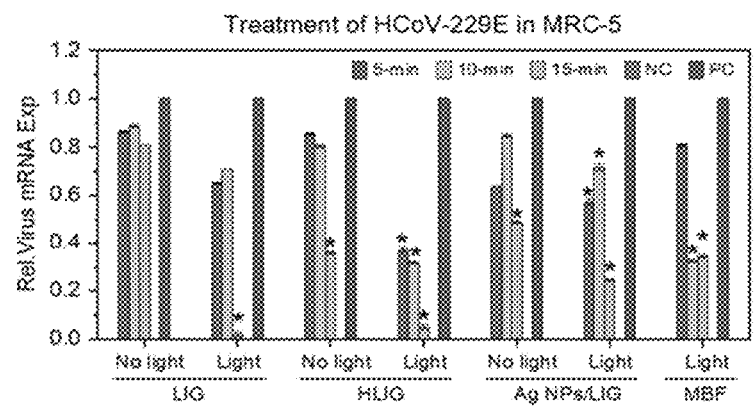
FIG. 7B shows anti-viral effect of different LIG membranes on MRC-5 cells infected with HCoV-229E.
Figure 7C:
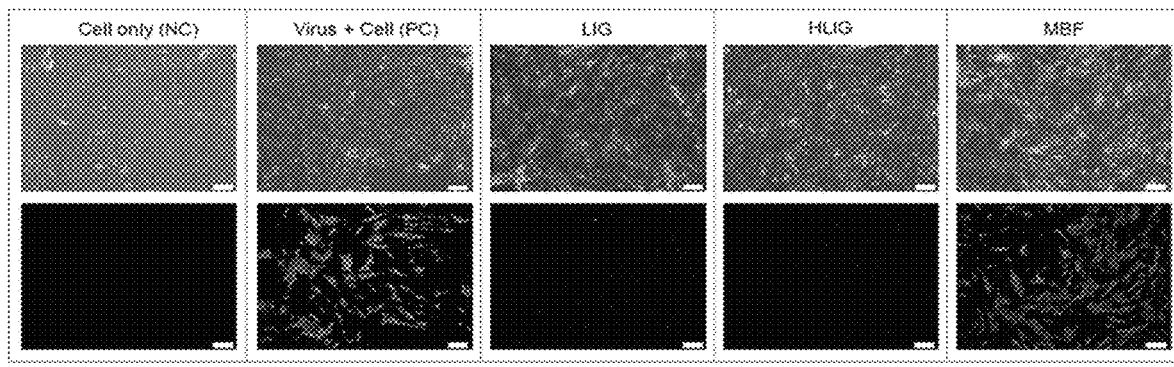
FIG. 7C shows immunofluorescence of MRC-5 cells infected with HCoV-OC43. the scale bar=50 um.
Figure 7D:
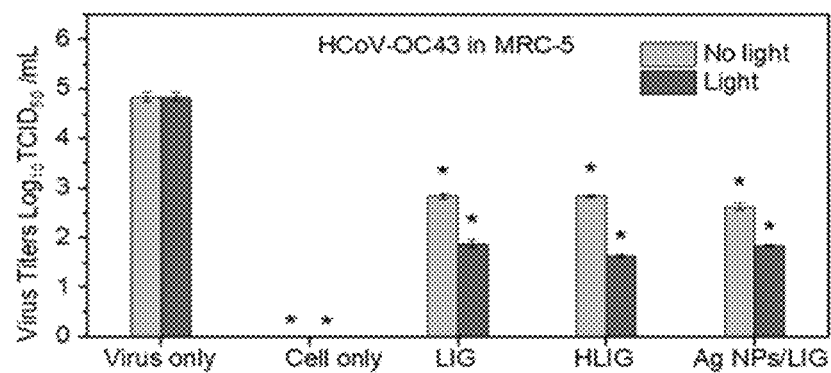
FIG. 7D shows titers of the HCoV-OC43 in MRC-5 cells.
Figure 7E:
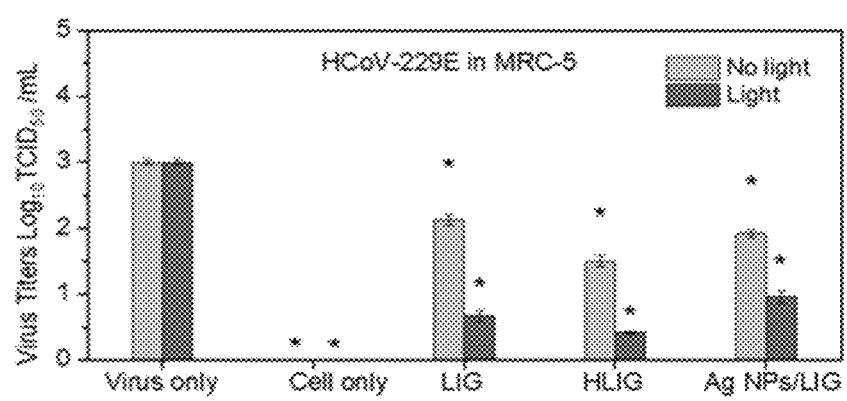
FIG. 7E shows titers of the HCoV-229E in MRC-5 cells.

Furthermore, two human coronaviruses, HCoV-OC43 and HCoV-229E, were used to evaluate the antiviral performance of three different types of LIG and melt-down fabrics (MBF), which are the key filtering layer in commercial surgical masks. The antiviral effect of LIG, HLIG, Ag NPs/LIG, and MBF was comprehensively evaluated from the nucleic acid (FIGS. 7A-7B), protein expression (FIG. 7C) and virus titers (FIGS. 7D-7E) of two coronaviruses HCoV-OC43 and HCoV-229E. Data were expressed as mean+SE, n=3, *p<0.05. According to the above results, it can be seen that all of the LIG, HLIG and LIG membranes with Ag show better antiviral activity than the MBF film.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

INDUSTRIAL APPLICABILITY

The present wirelessly-charged masks or respirators exhibit significant advantages in terms of the highly antiviral, long-lasting, reusable, self-cleaning, self-disinfecting, lightweight, portable, wireless-charged and comfortable, which serve as personal protective equipment to protect worldwide health care workers. Besides, low base cost, low maintenance cost, low operation cost, long lifetime easy and fast assembling procedures, and environmentally friendly materials are also very competitive and superior advantages.

The present wirelessly-charged masks or respirators can be used in a number of high-risk areas, including hospitals, airplanes, aging centers, makeshift hospitals and airports, and the potential buyers and customers can be well defined into four distinguished types: personal healthcare workers, hospitals, government sectors and humanitarian aid groups.

The invention claimed is:

1. A wireless rechargeable and portable anti-microbial respirator, comprising:
   a face-piece with an air inlet and an air outlet;
   a first belt and a second belt, wherein the first belt is connected to ends of the face-piece, and the second belt is configured to wrap around the waist of a user;
   a flexible outlet tube, wherein the first end of the flexible outlet tube is connected to the air outlet of the face-piece;
   a flexible intake tube wherein the first end of the flexible intake tube is connected to the air inlet of the face-piece; and
   a filtration system fixed onto the second belt, wherein the filtration system comprises:
      a housing;
      a first chamber located in the housing, configured to permit exhaled air to flow into the filter system, wherein the first chamber comprises a first channel connected to the second end of the flexible outlet tube, and an upper part of the first chamber is covered by a plate with a plurality of meshes such that only the first channel is exposed, and the meshes are configured to allow fresh airflow to flow into the first chamber;
      a second chamber located in the housing, configured to permit purified air to flow out of the filter system, wherein the second chamber comprises a second channel connected to the second end of the flexible intake tube, the second chamber further including a light panel and a fan unit; and the first chamber and the second chamber are separated by a filter unit;
      a third chamber located in the housing, wherein the third chamber includes a rechargeable battery, an electric motor and a wireless power transfer receiving apparatus,
   wherein the respirator is configured such that when the exhaled airflow and the fresh airflow flow into the first chamber and are then filtered by the filter unit, the filtered airflow flows into the second chamber and is sterilized by the light panel, and
   wherein the rechargeable battery provides power for the electric motor, and the fan unit is driven by the electric motor.

2. The wireless rechargeable and portable anti-microbial respirator of claim 1, wherein the filter unit is selected from a graphene filter, a bismuth vanadate ($BiVO_4$) filter, or a high efficiency particulate air (HEPA) filter containing at least one ultraviolet-A (UV-A) LEDs and titanium dioxide ($TiO_2$) nanoparticles-coated fiber.

3. The wireless rechargeable and portable anti-microbial respirator of claim 2, wherein the graphene filter further comprising:
   two layers of laser induced graphene (LIG) membranes, wherein a first of the two layers of LIG membranes serves as a positive electrode and a second of the two layers of LIG membranes serves as a negative electrode; and
   a porous dielectric layer positioned between the two layers of LIG membranes serving as an intermediate layer,
   wherein the rechargeable battery is connected to the two layers of LIG membranes with one or more wires,
   wherein the two layers of LIG membranes and the porous dielectric layer form a parallel plate capacitor, and the rechargeable battery provides the parallel plate capacitor with voltage.

4. The wireless rechargeable and portable anti-microbial respirator of claim 3, wherein the voltage in the parallel plate capacitor is in range of 0.5V to 3V.

5. The wireless rechargeable and portable anti-microbial respirator of claim 2, wherein the $BiVO_4$ filter further comprises at least five filtering layers, wherein the at least five filtering layers include a non-woven layer, an anti-adhesion layer, an activated carbon layer, a molten spray layer and a filter layer, wherein the $BiVO_4$ filter is coupled with a silver (Ag) or copper (Cu) nanoparticle-including layer.

6. The wireless rechargeable and portable anti-microbial respirator of claim 2, wherein the at least one UV-A LEDs has a UV light wavelength in a range of 315 nm to 400 nm.

7. The wireless rechargeable and portable anti-microbial respirator of claim 1, wherein the light panel further comprises one or more cluster LEDs and/or one or more wires connected to the rechargeable battery.

8. The wireless rechargeable and portable anti-microbial respirator of claim 1, wherein the shape of the filtration system is a cylinder with a diameter in a range of 50-150 mm and a height in a range of 50-100 mm.

9. The wireless rechargeable and portable anti-microbial respirator of claim 1, wherein the fan unit comprises a fan with a self-adjusting flowrate module.

10. The wireless rechargeable and portable anti-microbial respirator of claim 9, wherein the self-adjusting flowrate module comprises a pressure sensor and a CPU for calculating the required current of the electric motor, and the electric motor and the fan utilize the self-adjusting flowrate module to automatically adjust the rotating speed of the fan based on the pressure within the filtration system.

11. The wireless rechargeable and portable anti-microbial respirator of claim 10, wherein the rechargeable battery provides voltage for two layers of LIG membranes and the at least one UV-A LEDs.

12. The wireless rechargeable and portable anti-microbial respirator of claim 1, wherein the material used for the wireless power transfer receiving apparatus comprises one or more copper coils.

13. The wireless rechargeable and portable anti-microbial respirator of claim 1, wherein the face-piece covers a mouth and nose of a user.

14. The wireless rechargeable and portable anti-microbial respirator of claim 1, wherein the material of the face-piece is a silicone material.

15. The wireless rechargeable and portable anti-microbial respirator of claim 1, further comprising at least one one-way valve positioned at the junction between the face-piece and the first end of the flexible outlet tube and/or the first end of the flexible intake tube to prevent exhaled air with a higher carbon dioxide content from entering the face-piece again, and to prevent exhaled air from flowing directly into the ambient air.

16. The wireless rechargeable and portable anti-microbial respirator of claim 1, wherein the surfaces of both the flexible outlet tube and the flexible intake tube comprise graphene-based materials, bismuth vanadate ($BiVO_4$) coupled with silver (Ag) or copper (Cu) nanoparticles, or $TiO_2$-based materials.

17. The wireless rechargeable and portable anti-microbial respirator of claim 1, wherein the anti-microbial respirator is an anti-virus respirator or an anti-bacterial respirator.

18. The wireless rechargeable and portable anti-microbial respirator of claim 1, wherein both the flexible outlet tube and the flexible intake tube have an inner diameter of 12 mm and an outer diameter of 15 mm.

19. The wireless rechargeable and portable anti-microbial respirator of claim 18, wherein the flexible outlet tube and the flexible intake tube are further integrated into a sleeve.

* * * * *